United States Patent
Seiler et al.

(10) Patent No.: US 7,247,160 B2
(45) Date of Patent: Jul. 24, 2007

(54) APPARATUSES AND METHODS FOR PERCUTANEOUSLY IMPLANTING OBJECTS IN PATIENTS

(75) Inventors: Keith Seiler, Issaquah, WA (US); Eric Hadford, Snohomish, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 0 days.

(21) Appl. No.: 10/334,699

(22) Filed: Dec. 30, 2002

(65) Prior Publication Data

US 2004/0127765 A1 Jul. 1, 2004

(51) Int. Cl.
*A61B 17/32* (2006.01)

(52) U.S. Cl. .......................... 606/167; 600/7

(58) Field of Classification Search ............... 600/3, 600/7, 8, 4, 6; 604/60, 61, 64, 264, 57; 606/102, 606/130

See application file for complete search history.

(56) References Cited

U.S. PATENT DOCUMENTS

| | | | |
|---|---|---|---|
| 4,147,164 A | 4/1979 | Behney | |
| 4,787,384 A | 11/1988 | Campbell | |
| 5,002,548 A | 3/1991 | Campbell | |
| 5,024,727 A | 6/1991 | Campbell | |
| 5,074,318 A | 12/1991 | Campbell | |
| 5,279,554 A | 1/1994 | Turley | |
| D358,644 S | 5/1995 | Park | |
| 5,938,583 A | 8/1999 | Grimm | |
| 6,106,524 A | 8/2000 | Eggers | |
| 6,210,315 B1 * | 4/2001 | Andrews et al. | 600/7 |
| 6,267,718 B1 * | 7/2001 | Vitali et al. | 600/7 |
| 6,270,472 B1 * | 8/2001 | Antaki et al. | 604/61 |
| 6,450,938 B1 | 9/2002 | Miller | |
| 6,474,341 B1 | 11/2002 | Hunter | |
| 6,575,890 B2 | 6/2003 | Kaplan et al. | |

OTHER PUBLICATIONS

Author unknown, isosleeve system, downloaded from Internet Nov. 26, 2002, 2 pp., IMAGYN, brachytherapy, http://www.isosleeve.com/main/isosleeve/isoflash/index.htm.

Author unknown, RTP-6000 Precision Stabilizer, date unknown, 1 pg., Radiation Therapy Products, Seattle, Washington.

Author unknown, HDR Accessories, date unknown, 1 pg., Radiation Therapy Products, Seattle, Washington.

(Continued)

*Primary Examiner*—Gary Jackson
*Assistant Examiner*—Victor Nguyen
(74) *Attorney, Agent, or Firm*—Perkins Coie LLP

(57) ABSTRACT

Apparatuses and methods for percutaneously implanting objects, such as radioactive seeds or markers, in patients. In one embodiment, a device for percutaneously implanting an object in a patient includes a handle, a cannula projecting outwardly from the handle, and an actuator movably disposed relative to the handle. In one aspect of this embodiment, the cannula can be configured to releasably hold the object and percutaneously penetrate the patient. In another aspect of this embodiment, the actuator can be operably connected to the cannula and operable to move the cannula relative to the handle and release the object within the patient. In a further aspect of this embodiment, the cannula can include a tip portion having a restriction configured to releasably hold the object for implantation in the patient.

5 Claims, 8 Drawing Sheets

OTHER PUBLICATIONS

Author unknown, RTP BrachyPak™, © 2002, 2 pp., Radiation Therapy Products, Seattle, Washington.

Author unknown, Shielding Products, date unknown, 1 pg., Radiation Therapy Products, Seattle, Washington.

Author unknown, NLX 300 Needle Loader, © 2001, 1 pg., Radiation Therapy Products, Seattle, Washington.

International Search Report dated Aug. 23, 2004, PCT Application No. PCT/US03/41155.

* cited by examiner

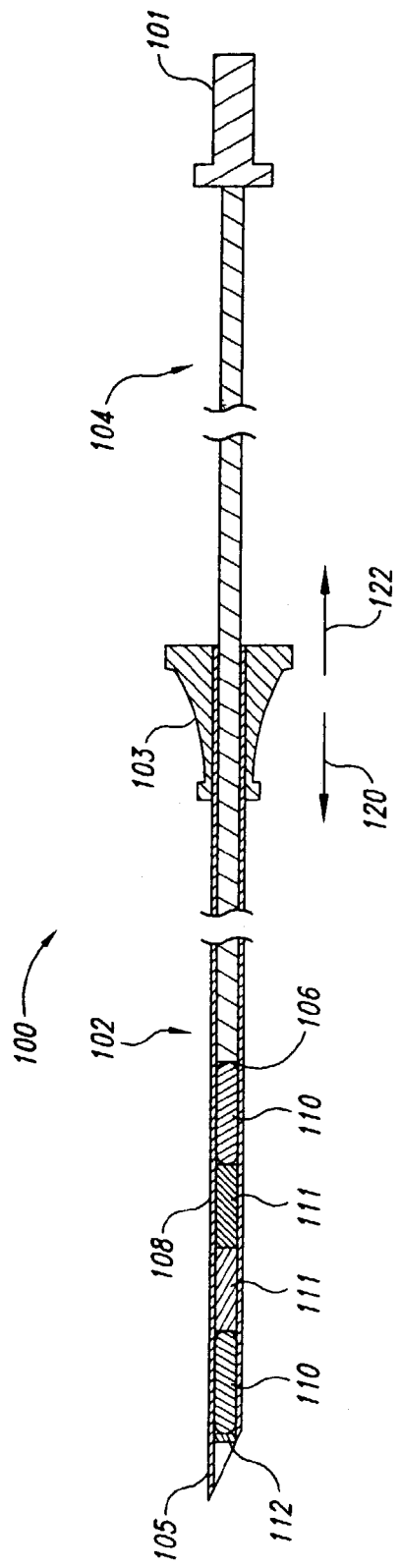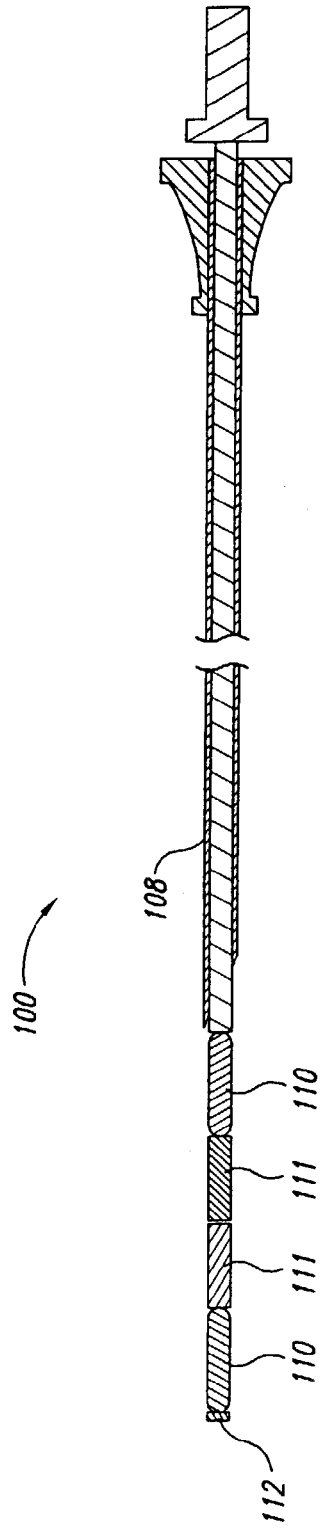
Fig. 1A (Prior Art)
Fig. 1B (Prior Art)

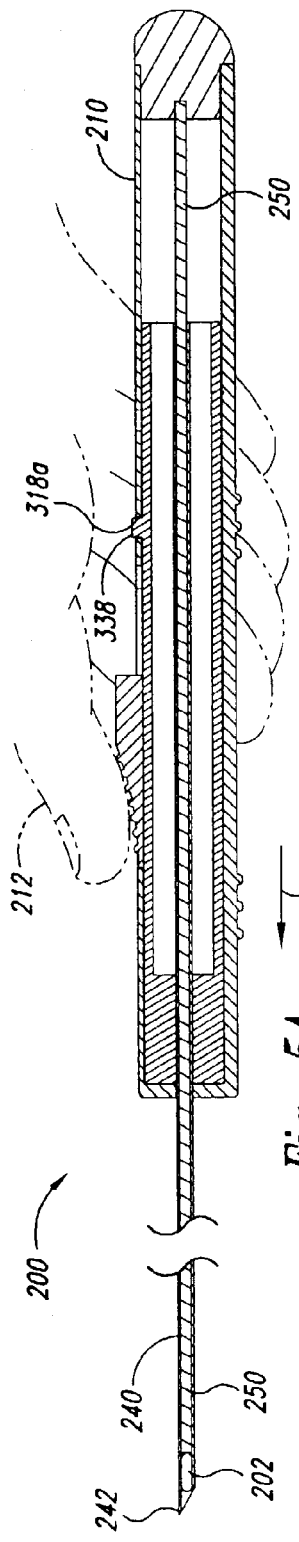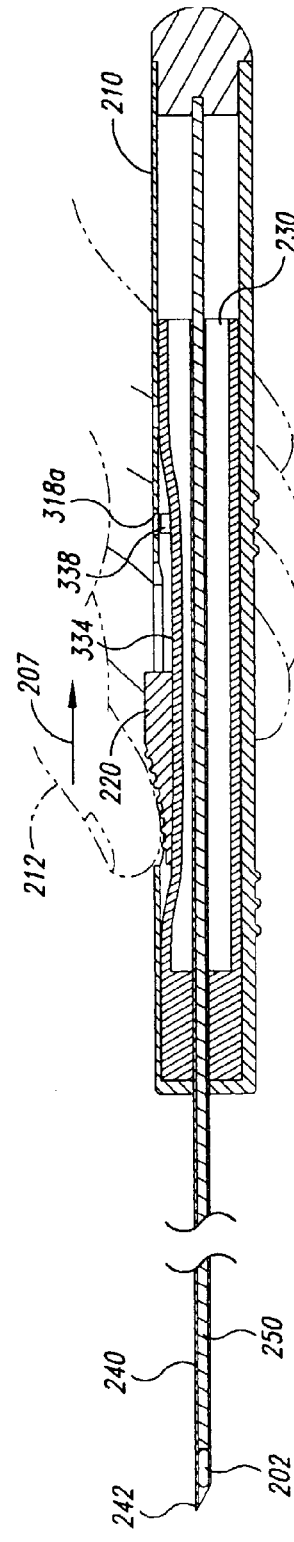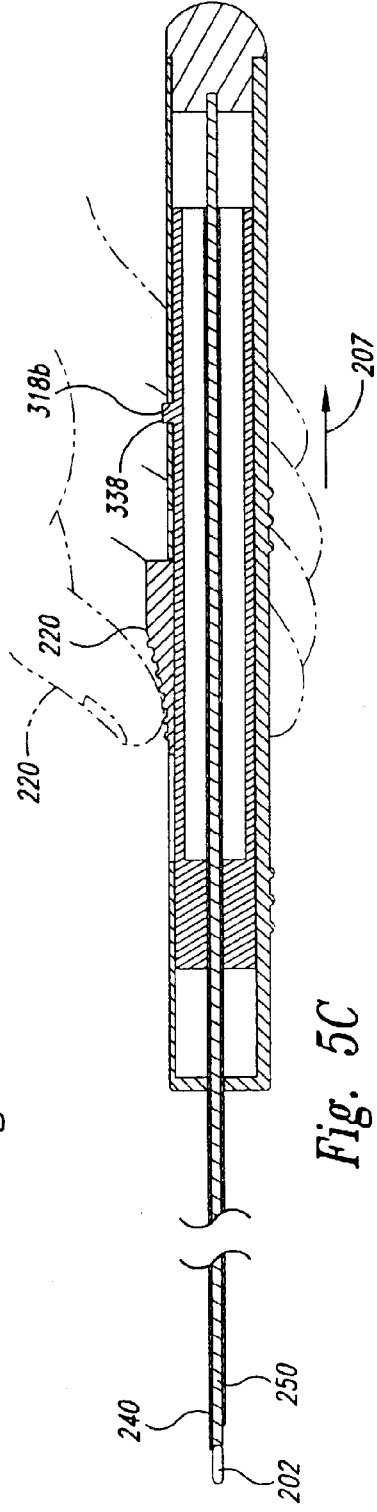

APPARATUSES AND METHODS FOR PERCUTANEOUSLY IMPLANTING OBJECTS IN PATIENTS

TECHNICAL FIELD

The following disclosure relates generally to medical devices for percutaneously implanting markers or other small objects in patients.

BACKGROUND

A number of existing medical treatments involve percutaneously inserting or implanting objects in a patient. One such treatment is brachytherapy for prostate cancer. In brachytherapy, radioactive sources or "seeds" are implanted relative to a tumor to provide a high dose of radiation to the tumor but not the surrounding healthy tissue. Other oncological treatments involve percutaneously implanting radioopaque markers or signal-generating markers adjacent to the tumor. The markers identify the location of the tumor so that a high dose of radiation from a linear accelerator or other external source can be focused directly at the tumor.

FIGS. 1A and 1B are cross-sectional views of a two-piece introducer 100 of the prior art. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a cannula 108 extending through the second handle 103. The cannula 108 is configured to hold radioactive seeds 110 or other objects. The cannula 108 has a distal tip 105 configured to percutaneously penetrate the patient for implantation of the seeds 110 in the patient. Inert spacers 111 can be used to provide the desired spacing between the seeds 110 when the seeds 110 are implanted in the patient. The seeds 110 and spacers 111 are retained in the cannula 108 by a plug 112 made from bone wax or other suitable bio-compatible materials.

To implant the seeds 110 at a target location in a patient (not shown) in the desired pattern as loaded in the cannula 108, an operator (also not shown) pushes the cannula 108 in a first direction 120 to insert the tip 105 into the patient. The operator then pushes the second handle 103 further in the first direction 120 to position the tip 105 at the desired depth within the patient where the seeds 110 are to be released. Throughout this motion, the operator moves the needle 102 and the stylet 104 together as a unit. At the desired depth, the operator grasps the first handle 101 with one hand and the second handle 103 with the other hand and, while holding the first handle 101 stationary, slides the second handle 103 back in a second direction 122 toward the first handle 101. As shown in FIG. 1B, this movement causes the cannula 108 to pull back from the plug 112, the seeds 110, and the spacers 111 to implant them in the patient.

One shortcoming of the prior art introducer 100 is that the two-handed movement required to properly release the seeds 110 at the target location and in the desired pattern may be somewhat awkward and nonintuitive. As a result, the operator is prone to err and may inadvertently misplace the seeds 110. For example, to properly release the seeds 110, the operator must hold the first handle 101 stationary while sliding the second handle 103 back in the second direction 122 toward the first handle 101. If, instead, the operator accidentally pushes the first handle 101 toward the second handle 103, then the stylet 104 may push the seeds 110 out of the cannula 108 in the first direction 120. This movement could cause the seeds 110 and the spacers 111 to collide in a "train wreck" just beyond the tip 105 of the cannula 108. Either way, the seeds will not be positioned accurately relative to the target location or in the desired pattern. A further shortcoming of the prior art introducer 100 is that the bone wax used for the plug 112 in brachytherapy applications may melt prematurely allowing the seeds 110 to migrate out of the cannula 108 before reaching the desired target location. As such, conventional introducers for brachytherapy applications are custom loaded at the treatment facility and are not suitable for being transported in warm environments.

SUMMARY

The invention is directed to apparatuses and methods for implanting markers, radioactive seeds or other small objects in patients. In one aspect, a device for percutaneously implanting an object in a patient includes a handle, a cannula projecting outwardly relative to the handle, and an actuator operably connected to the cannula and movably disposed relative to the handle. The cannula can have a proximal portion positioned proximate to the handle and a distal portion configured to releasably hold the object and percutaneously penetrate the patient by movement of the handle. The actuator can be operable to slide the cannula relative to the handle and release the object within the patient.

In another aspect, the device can further include a stylet extending at least partially within the cannula and being fixedly positioned with respect to the handle. Operating the actuator to slide the cannula relative to the handle causes the cannula to slide relative to the stationary stylet and release the object within the patient.

In a further aspect, the cannula can include a tip portion having a restriction configured to releasably hold the object for implantation in the patient, and the actuator can be selectively movable from a first position to a second position. When the actuator is in the first position, the tip portion of the cannula can at least generally retain the object. When the actuator is in the second position, the cannula can be drawn back from the object to overcome the restriction and release the object within the patient.

In yet another aspect, a method for percutaneously implanting an object in a patient includes moving a handle to percutaneously insert a cannula projecting from the handle within the patient, and moving the cannula relative to the handle to release the object within the patient. Moving the cannula relative to the handle can include sliding the cannula with respect to a stationary stylet extending coaxially through at least a portion of the cannula. Moving the handle to percutaneously insert the cannula can include driving the handle forward with a hand of an operator. Further, moving the cannula relative to the handle to release the object within the patient can include manipulating an actuator with a digit of the hand of the operator to move the cannula aft relative to the handle while the handle remains stationary in the hand of the operator.

BRIEF DESCRIPTION OF THE DRAWINGS

FIGS. 1A and 1B are cross-sectional views of a two-piece introducer of the prior art.

FIGS. 5A–C are enlarged cross-sectional views of the introducer shown in FIGS. 2A and 2B illustrating operation of an actuator in accordance with embodiments of the invention.

DETAILED DESCRIPTION

Figure 2A:
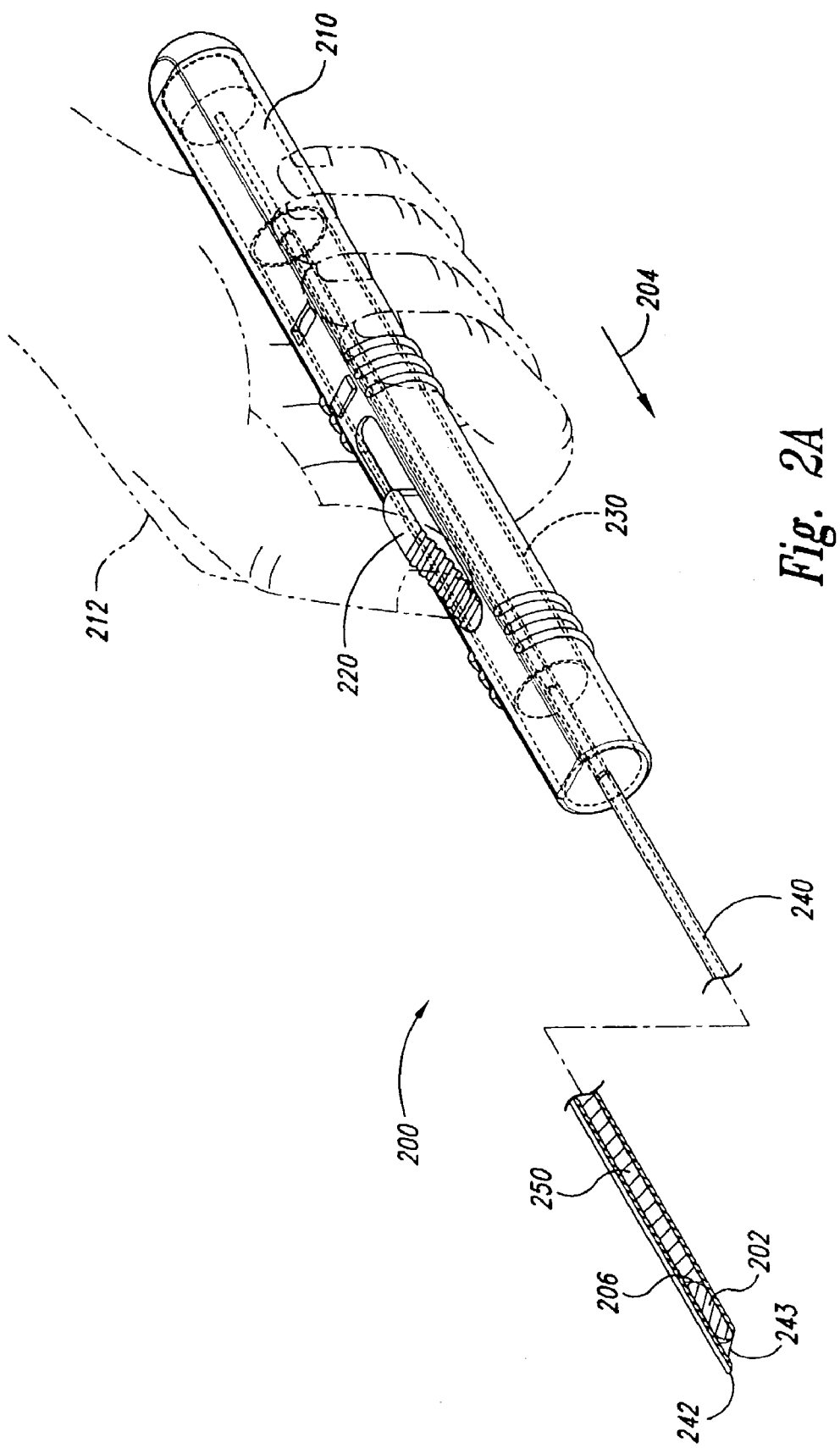
FIGS. 2A and 2B are hidden isometric views of an introducer in accordance with an embodiment of the invention with a distal portion of the introducer shown in cross-section.

The following disclosure describes medical devices and methods for percutaneously implanting objects, such as radioactive seeds or markers, in patients. Certain specific details are set forth in the following description and in FIGS. 2A–6B to provide a thorough understanding of various embodiments of the invention. Certain well-known details often associated with such medical devices are not set forth in the following disclosure to avoid unnecessarily obscuring the various embodiments of the invention. Further, those of ordinary skill in the relevant art will understand that they can practice other embodiments of the invention without several of the details described below.

In the drawings, identical reference numbers identify identical or at least generally similar elements. To facilitate the discussion of any particular element, the most significant digit or digits of any reference number refer to the figure in which that element is first introduced. For example, element 210 is first introduced and discussed with reference to FIG. 2A.

Figure 2B:
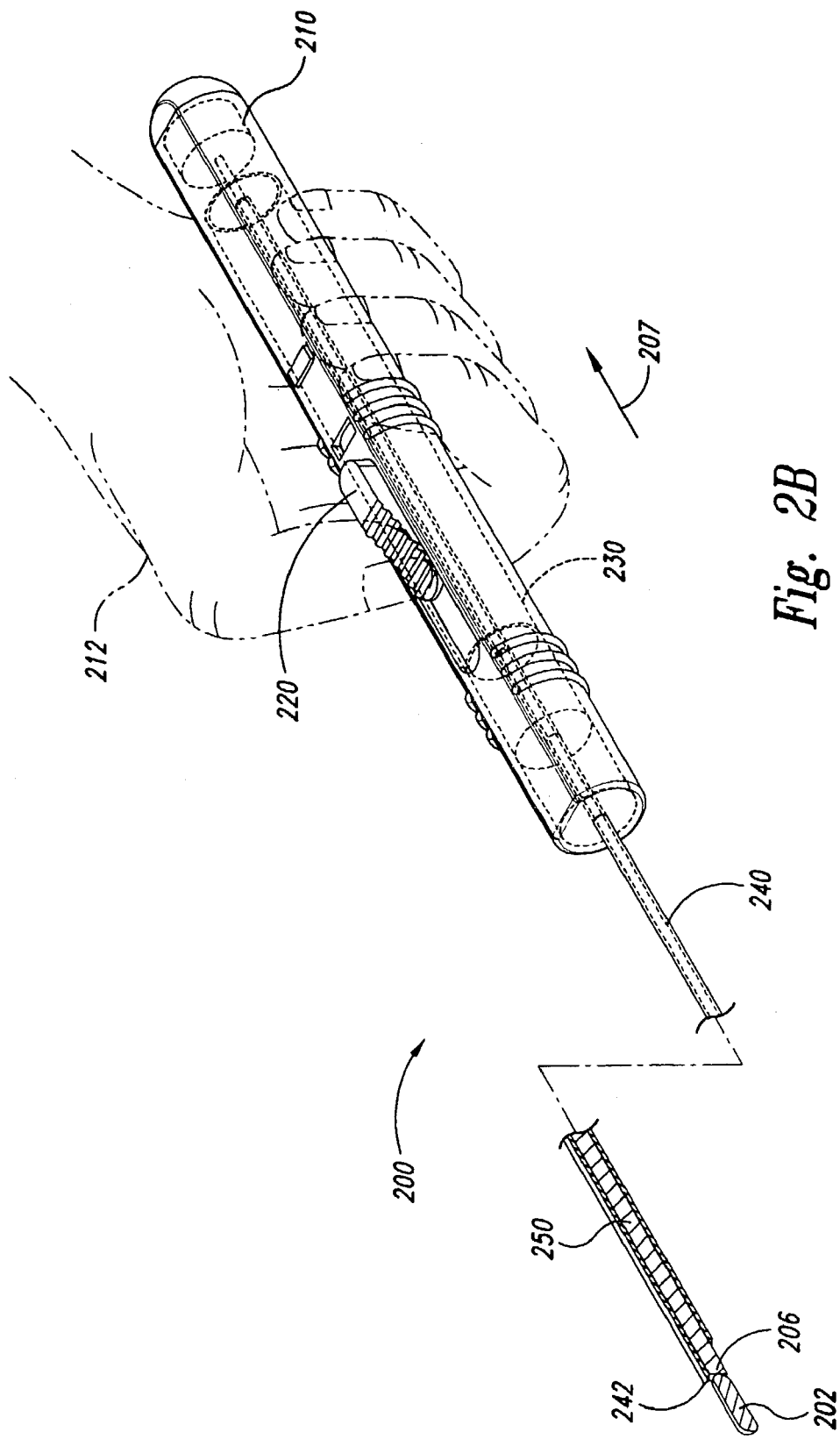

FIGS. 2A and 2B are hidden isometric views of an introducer 200 in accordance with an embodiment of the invention with a distal portion of the introducer being cut-away. Referring first to FIG. 2A, one embodiment of the introducer 200 includes a handle 210, a hollow needle or cannula 240 projecting outwardly from the handle 210, and an actuator 230 fixedly attached to the cannula 240 and movably disposed within the handle 210. The cannula 240 has a proximal portion slidably disposed within the handle 210 and a distal tip portion 242. The cannula 240 can be a 14 gauge needle or smaller in many applications. The introducer 200 also includes a stylet 250 extending coaxially within the cannula 240. The stylet 250 can be fixedly attached relative to the handle 210 and can include a blunt distal end 206. The actuator 230 can include a button 220 manually operable to move the actuator 230 and the cannula 240 fore and aft with respect to the stylet 250 using a digit of a single hand.

A signal-generating marker 202, a radio-active seed or other implantable object is slidably positioned in the cannula 240 between the distal end 206 of the stylet 250 and the tip portion 242 of the cannula 240. The tip portion 242 can be configured to percutaneously penetrate the patient for implantation of the marker 202, and can include a restriction 243 configured to releasably retain the marker 202 in the cannula 240 prior to release of the marker 202 in the patient. In other embodiments, the cannula 240 can hold other objects for implantation in the patient in addition to the marker 202. For example, in another embodiment, the cannula 240 can hold additional markers optionally spaced apart by one or more spacers to provide a desired marker pattern. Similarly, in a further embodiment, the cannula 240 can hold a plurality of radioactive seeds optionally spaced apart by one or more spacers to provide a desired seed pattern.

To percutaneously implant the marker 202 in a patient (not shown), an operator 212 grasps the handle 210 in one hand and aligns the cannula 240 with a desired point of entry on the patient. The operator 212 then moves the handle 210 in a forward direction 204 to position the tip portion 242 of the cannula 240 at the target location within the patient (for example, proximate to a tumor). During this movement, the cannula 240 is held stationary relative to the stylet 250. Referring next to FIG. 2B, after the tip portion 242 is at the target location, the operator 212 uses a single hand to move the button 220 in an aft direction 207 relative to the handle 210 and hold the stylet 250 stationary relative to the handle 210. This movement draws the cannula 240 back in the aft direction 207 over the marker 202 and the stylet 250. The stylet 250 is fixed to the handle 210 and remains stationary so that the marker 202 is implanted in the patient as the cannula 240 moves aftward. The operator 212 can now move the handle 210 in the aft direction 207 to retract the cannula 240 from the patient.

One feature of embodiments of the introducer 200 shown in FIGS. 2A and 2B is that the operator can accurately release the marker 202 in the patient by a single movement of a digit of one hand. More specifically, because the stylet 250 is fixed to the handle 210 and the actuator 230 is operated by the operator's hand that holds the handle 210, the stylet 250 cannot push the markers out of the cannula 240. An advantage of this feature is that the required movement is intuitive and simple to execute, thus avoiding the possibility of driving the markers out of the cannula causing a "train wreck." In contrast, the prior art introducer 100 of FIGS. 1A and 1B requires a potentially awkward two-handed movement to properly release objects at a target location within a patient. The intuitive movement of the prior art device is to move the handles 101 and 103 (FIG. 1A) toward each other. As a result, an operator of the prior art introducer 100 is prone to err and may inadvertently misplace the objects.

Figure 3:
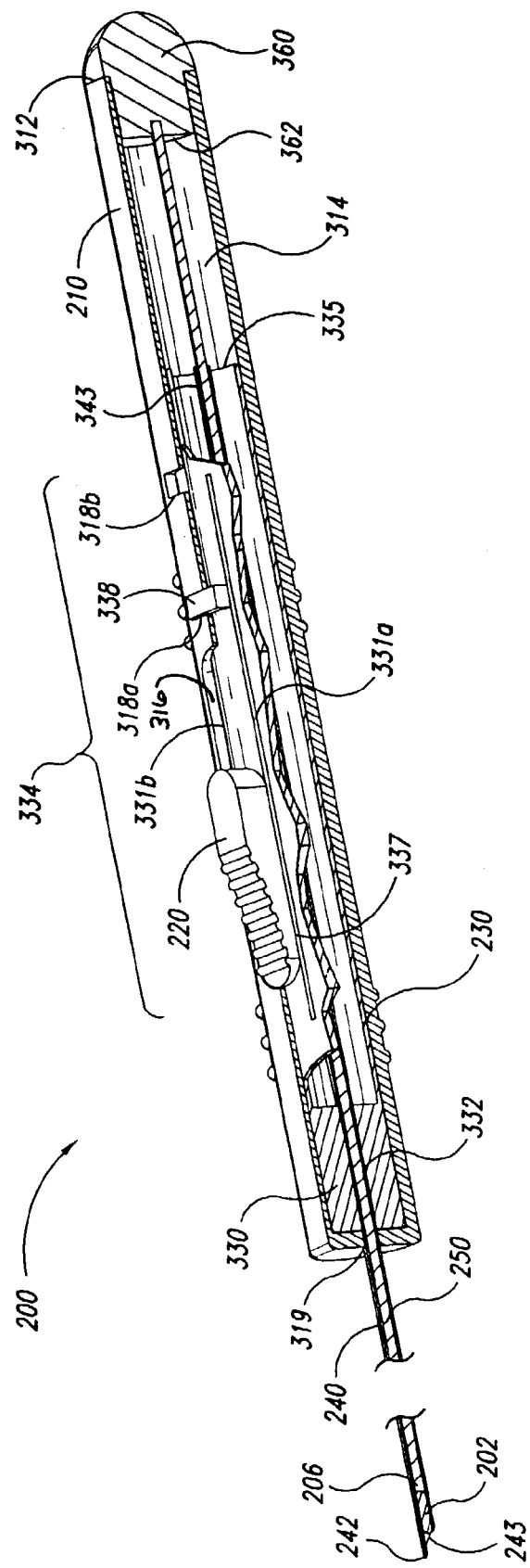
FIG. 3 is a cut-away isometric view of the introducer shown in FIGS. 2A and 2B in accordance with an embodiment of the invention with a portion of the introducer shown in cross-section.

FIG. 3 is a cross-sectional isometric view of the introducer 200 shown in FIGS. 2A and 2B in accordance with an embodiment of the invention. In one aspect of this embodiment, the stylet 250 is fixedly attached to an end cap 360. The end cap 360 can include an engagement portion 362 configured to be received in a handle opening 312 in the handle 210. In the illustrated embodiment, the distal end 206 of the stylet 250 can be at least generally blunt. In other embodiments, the distal end 206 can have other shapes depending on the particular application. For example, in other embodiments, the distal end 206 can have a beveled or pencil-point shape.

In another aspect of this embodiment, the actuator 230 is at least generally hollow and includes a body 330, a bore 332 through the body 330, a position selector 334, and an opening 335 at one end of the body 330 opposite the bore 332. A proximal end of the cannula 240 is positioned in the bore 332 and fixedly attached to the body 330. The cannula 240 can extend from the opening 335 and project outwardly from the bore 332. The position selector 334 of the illustrated embodiment includes an indexing feature or protruding tab 338 and a button pad 337 for mounting the button 220. First and second slits 331a and 331b are positioned on opposite sides of the position selector 334 and allow the protruding tab 338 to deflect resiliently inward in response to depression of the button 220.

In a further aspect of this embodiment, the handle 210 is at least generally hollow and includes an interior portion 314 and a cannula opening 319. The interior portion 314 can be configured to slidably receive the actuator 230, and the cannula opening 319 can be configured to allow the cannula 240 to slide freely back and forth with respect to the handle 210 as the actuator 230 moves back and forth within interior portion 314 of the handle 210.

In yet another aspect of this embodiment, the handle 210 further includes a button opening 316 and locking features 318. In the illustrated embodiment, the locking features 318 include a first tab opening 318a and a second tab opening 318b. The locking features 318 can be configured to selectively receive the protruding tab 338 of the position selector 334 as the operator (not shown) moves the position selector 334 fore and aft in the handle 210 with the button 220. As will be explained in greater detail below, in other embodiments, the handle 210 can include more locking features depending on the number of markers 202 or other objects the introducer 200 is configured to implant.

The introducer 200 can be assembled by inserting the cannula 240 through the handle opening 312 and the cannula opening 319 until the button pad 337 is aligned with the button opening 316 and the protruding tab 338 engages the first locking feature 318a. The button 220 is then fixedly attached to the button pad 337. The marker 202 can then be inserted into the cannula 240 through a cannula inlet 343 at the proximal end of the cannula 240. In other embodiments, the marker 202 can be inserted into the distal end of the cannula. The cannula inlet 343 can be flared or otherwise configured for smooth loading of the marker 202 or other objects, such as seeds and/or spacers. The distal end 206 of the stylet 250 is then inserted into the cannula inlet 343 and moved through the cannula 240 driving the marker 202 through the cannula 240 until the engagement portion 362 of the cap 360 mates with the handle opening 312. At this point the marker 202 is releasably held in the cannula 240 between the distal end 206 of the stylet 250 and the restriction 243 of the tip portion 242.

Figure 4A:
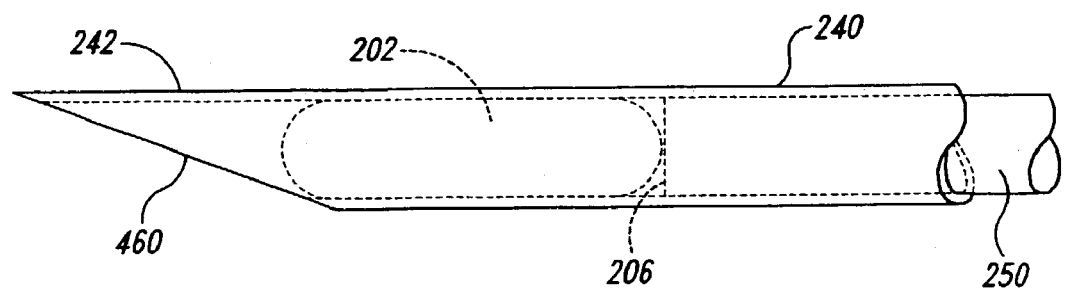
FIGS. 4A and 4B are enlarged hidden side and bottom views, respectively, of a tip portion of a cannula in accordance with an embodiment of the invention.
Figure 4B:
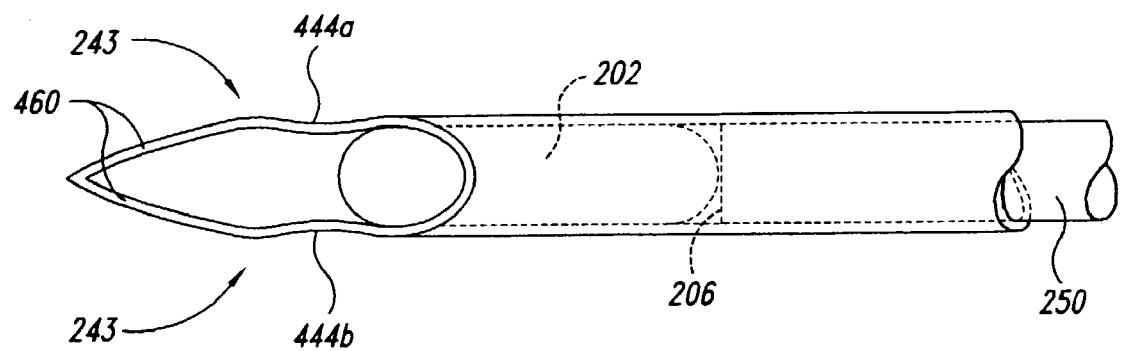

FIGS. 4A and 4B are enlarged hidden side and bottom views, respectively, of the tip portion 242 of the cannula 240 in accordance with an embodiment of the invention. Referring first to FIG. 4A, in one aspect of this embodiment, the tip portion 242 includes a beveled edge 460 configured to facilitate percutaneous penetration of the patient. In other embodiments, the tip portion 242 can have other configurations for facilitating percutaneous penetration. For example, in another embodiment, the tip portion 242 can include a double-beveled edge.

Referring now to FIG. 4B, in another aspect of this embodiment, the restriction 243 includes a first crimp 444a and a second crimp 444b formed in the beveled edge 460. The crimps 444 can be shaped and sized to reduce the width of the cannula 240 to be less than the diameter of the marker 202. This reduction in width can be tailored to provide a small resistance sufficient to retain the marker 202 in the cannula 240 until the tip portion 242 moves aft over the distal end 206 of the stylet 250. The restriction can be further tailored to provide the required resistance without scratching or otherwise damaging the marker 202 or, as the case may be, other objects such as radio-active seeds that can be implanted with the introducer 200 (FIGS. 2A and 2B). In other embodiments, other types of restrictions can be used to releasably retain the marker 202 in the cannula 240. For example, in another embodiment, the restriction can include only a single crimp on one side of the cannula 240. In a further embodiment, the restriction can include material added to the tip portion 242 proximate to the beveled edge 460, such as weld material or cured adhesive. In yet another embodiment, the restriction can include a feature machined or otherwise formed into the tip portion 242 proximate to the beveled edge 460.

One feature of embodiments of the invention shown in FIGS. 4A–B is that the restriction 243 is only slightly smaller than the outside diameter of the marker 202. An advantage of this feature is that the restriction 243 provides tactile feedback to the operator (not shown) as the tip portion 242 retracts over the marker 202. Such tactile feedback provides an indication to the operator that the marker 202 has been released within the patient. This feature can be advantageous when the introducer 200 is used to sequentially implant a plurality of objects, such as a plurality of markers, at different depths within the patient. Another feature of embodiments of the invention shown in FIGS. 4A–B is that the restriction is positioned at least proximate to and often at the beveled edge 460. An advantage of this feature is that the beveled edge 460 provides a spring-back effect that further enhances the tactile feedback provided to the operator of the introducer 200.

Yet another feature of embodiments of the invention shown in FIGS. 4A–B is that the restriction 243 avoids the use of bone wax or other materials used in the prior art to hold the marker 202 in the cannula 240 prior to release. An advantage of this feature is that these other materials can melt or otherwise fail prematurely allowing the marker 202 to migrate out of the cannula 240 prior to reaching the target location. In contrast, the restriction 243 provides an environmentally stable solution that is not susceptible to fluctuating temperatures. Another advantage is that bone wax is not inadvertently introduced into a patient.

FIGS. 5A–C are enlarged cross-sectional views of the introducer 200 illustrating operation of the position selector 334 in accordance with embodiments of the invention. FIG. 5A shows the introducer 200 configured for insertion of the cannula 240 into the patient to implant the marker 202. In this mode, the protruding tab 338 of the position selector 334 engages the first locking feature 318a on the handle 210, thus holding the cannula 240 stationary relative to the stylet 250. In FIG. 5B, the tip portion 242 is at the target location within the patient and the operator 212 depresses the button 220 causing the protruding tab 338 to disengage from the first locking feature 318a. The operator 212 now moves the button 220 in the aft direction 207 sliding the actuator 230 aft in the handle 210. As shown in FIG. 5C, sliding the actuator 230 aft in the handle 210 draws the cannula 240 back over the stationary stylet 250 releasing the marker 202 in the patient. The operator 212 now releases the button 220 allowing the protruding tab 338 to engage the second locking feature 318b. The operator 212 can now retract the cannula 240 from the patient.

Those of ordinary skill in the relevant art will recognize that the structures described above for controlling the position of the cannula 240 relative to the stylet 250 (such as the position selector 334, the button 220, the protruding tab 338, and the locking features 318) represent but one embodiment of the present invention. Accordingly, in other embodiments, the features described above can have other details without departing from the spirit or scope of the invention. For example, in another embodiment, the protruding tab 338 and the locking features 318 can be omitted and the position of the actuator 230 can be manually controlled by the operator 212 or can be controlled by a friction surface, such as a serrated surface, existing between the actuator 230, and the handle 210.

Figure 6:
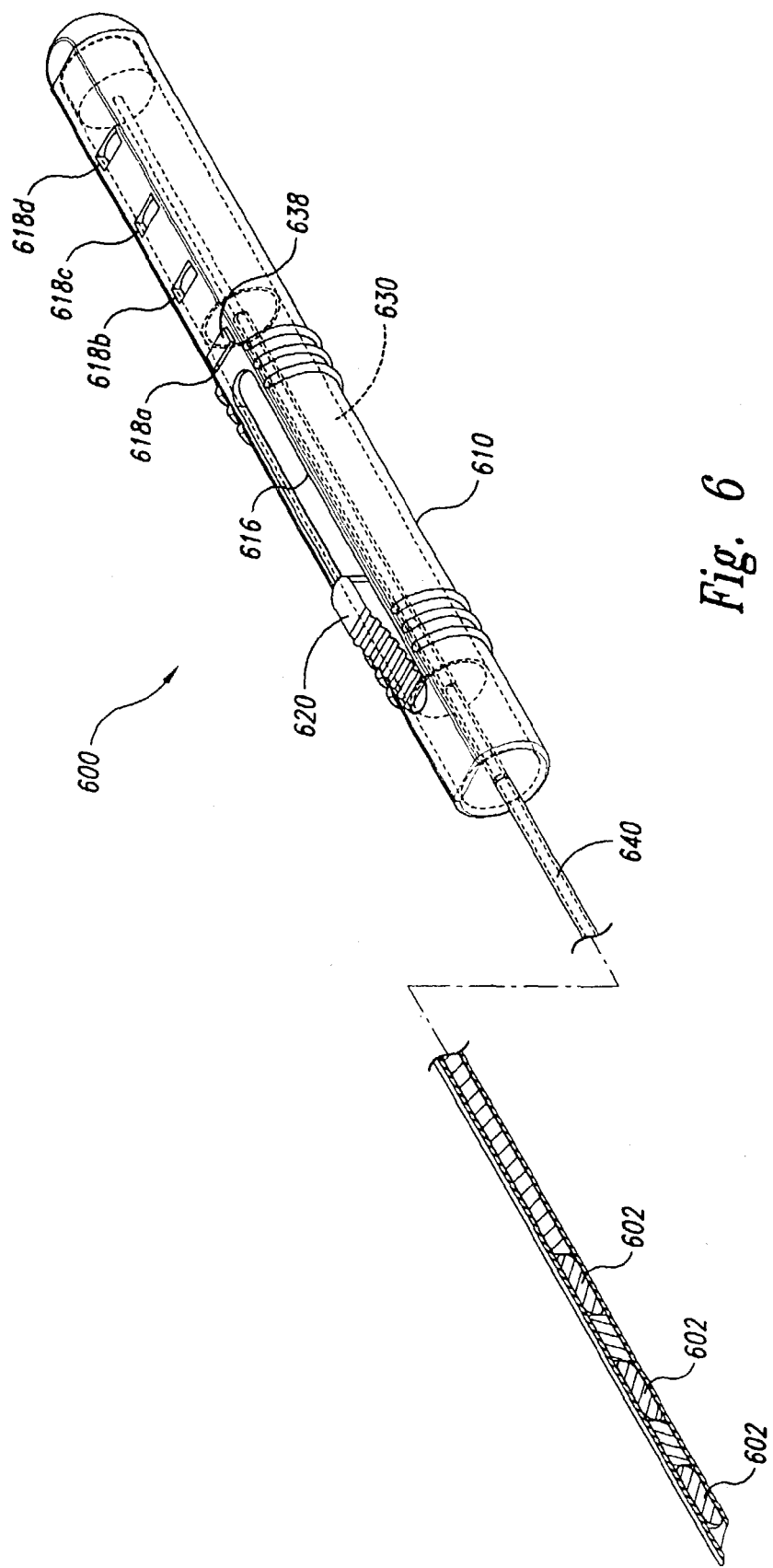
FIG. 6 is a hidden isometric view of an introducer in accordance with another embodiment of the invention with a distal portion of the introducer shown in cross-section.

FIG. 6 is a hidden isometric view of an introducer 600 in accordance with another embodiment of the invention with a distal portion of the introducer shown cut-away. In one aspect of this embodiment, the introducer 600 includes a handle 610, a cannula 640 projecting outwardly from the handle 610, and an actuator 630 fixedly attached to the cannula 640 and movably disposed within the handle 610. The handle 610, the cannula 640, and the actuator 630 can be at least approximately similar in structure and function to their counterparts of the introducer 200 described above with reference to FIGS. 2A–5C. In another aspect of this embodiment, however, the handle 610 includes an elongated button opening 616 and a plurality of locking features 618 (shown as a first tab opening 618a, a second tab opening 618b, a third tab opening 618c, and a fourth tab opening 618d). The locking features 618 are configured to selectively receive a protruding tab 638 projecting from the actuator 630.

In another aspect of this embodiment, a plurality of markers 602 are slidably positioned in the cannula 640. Accordingly, an operator (not shown) can sequentially release the markers 602 in a patient (also not shown) by sequentially depressing a button 620 and moving the button 620 aft relative to the handle 610. With each aft movement, the protruding tab 638 is selectively received by one of the locking features 618. In this manner, the operator can monitor and control the timing of each marker release. The operator, for example, can implant a first marker 602 at a first target location, reposition the introducer 600, and implant a second marker 602 at a second location without having to reload the introducer 600.

Figure 7:
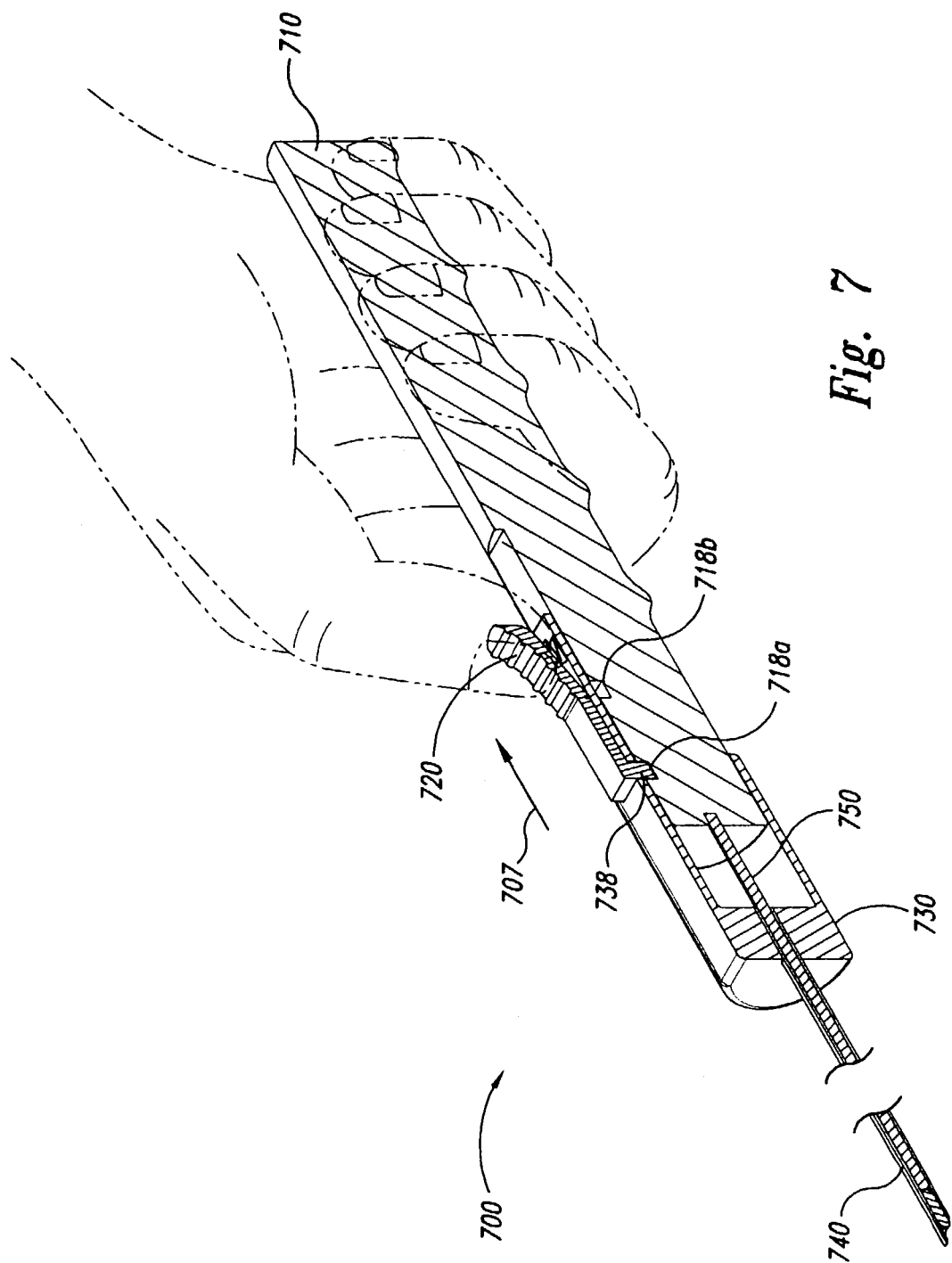
FIG. 7 is a cross-sectional isometric view of an introducer having an external actuator in accordance with another embodiment of the invention.

FIG. 7 is a cross-sectional isometric view of an introducer 700 having an external actuator 730 in accordance with another embodiment of the invention. In one aspect of this embodiment, the introducer 700 includes a cannula 740 projecting outwardly relative to a handle 710. The cannula 740 is fixedly attached to the actuator 730, and the actuator 730 is slidably disposed over at least a portion of the handle 710. The introducer 700 further includes a stylet 750 fixedly attached to the handle 710 and extending coaxially within the cannula 740. In another aspect of this embodiment, the actuator 730 can include a rocker-button 720 with a protruding tab 738 configured to be selectively received in locking features 718 of the handle 710 (shown as a first locking feature 718a and a second locking feature 718b). Depressing the rocker-button 720 can disengage the protruding tab 738 from the first locking feature 718a and allow the actuator 730 to be slid aft in direction 707 relative to the handle 710. This action causes the cannula 740 to slide aft over the marker 202 and the stationary stylet 750 releasing the marker 202.

Although specific embodiments of, and examples for, the present invention are described herein for illustrative purposes, various modifications can be made without departing from the spirit and scope of the invention as will be readily apparent to those of ordinary skill in the relevant art. For example, although introducers are described above for implanting wireless objects, such as radioactive seeds or resonating activatable markers, the teachings of the present invention can also be applied to introducers for implanting markers that are hard-wired to a power source external to the patient. In these embodiments, for example, a suitable hole or other outlet can be provided in the introducer handle as required to accommodate passage of the wire. In addition, although the present disclosure describes manual introducers, in other embodiments, powered introducers that are at least partially automated can also be configured in accordance with embodiments of the present invention.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A device for percutaneously implanting an object in a patient, the device comprising:
   a handle configured to be held in a single hand of an operator;
   a cannula having a proximal portion positioned proximate to the handle and a distal portion projecting outwardly relative to the handle, the cannula being axially movable with respect to the handle and configured to releasably hold the object and percutaneously penetrate the patient by movement of the handle;
   a stylet extending coaxially through at least a portion of the cannula and being fixedly attached to the handle; and
   an actuator movably disposed relative to the handle, wherein the actuator is configured to be manipulated by a digit of the hand of the operator while the handle is held stationary to slide the cannula relative to the handle and release the object within the patient wherein a position selector operably connected to the actuator, wherein the handle includes at least a first locking feature and a second locking feature offset from the first locking feature, wherein the first locking feature is configured to engage the position selector when the actuator is in a first position, and wherein the second locking feature is configured to engage the position selector when the actuator is in a second position.

2. The device of claim 1, further comprising a button operably connected to the actuator and configured to be manipulated by the digit of the single hand of the operator to slide the cannula relative to the stationary stylet and release the object within the patient.

3. The device of claim 1 wherein the distal portion of the cannula includes a tip portion configured to percutaneously penetrate the patient, wherein the tip portion is deformed to include a restriction configured to releasably retain the object between a distal end of the stylet and the restriction, and wherein the cannula is axially movable with respect to the stylet to overcome the restriction and release the object within the patient.

4. The device of claim 1 wherein the handle includes an interior portion and the actuator is slidably disposed at least partially within the interior portion of the handle.

5. The device of claim 1 wherein the actuator includes an interior portion and handle is slidably disposed at least partially within the interior portion of the actuator.

* * * * *

UNITED STATES PATENT AND TRADEMARK OFFICE
CERTIFICATE OF CORRECTION

| | |
|---|---|
| PATENT NO. | : 7,247,160 B2 |
| APPLICATION NO. | : 10/334699 |
| DATED | : July 24, 2007 |
| INVENTOR(S) | : Seiler et al. |

It is certified that error appears in the above-identified patent and that said Letters Patent is hereby corrected as shown below:

In column 3, line 58, delete "radio-active" and insert -- radioactive --, therefor.

In column 5, line 64, delete "radio-active" and insert -- radioactive --, therefor.

Signed and Sealed this

Eighth Day of July, 2008

JON W. DUDAS
*Director of the United States Patent and Trademark Office*